US 7,135,002 B2

(12) United States Patent
Sullivan

(10) Patent No.: US 7,135,002 B2
(45) Date of Patent: Nov. 14, 2006

(54) DETERMINING HEART RATE

(75) Inventor: Colin Edward Sullivan, Birchgrove (AU)

(73) Assignee: Sonomedical Pty Ltd, Balmain (AU)

( * ) Notice: Subject to any disclaimer, the term of this patent is extended or adjusted under 35 U.S.C. 154(b) by 115 days.

(21) Appl. No.: 10/475,571

(22) PCT Filed: Jan. 18, 2002

(86) PCT No.: PCT/AU02/00056

§ 371 (c)(1),
(2), (4) Date: Aug. 11, 2004

(87) PCT Pub. No.: WO02/058553

PCT Pub. Date: Aug. 1, 2002

(65) Prior Publication Data

US 2004/0267147 A1    Dec. 30, 2004

(51) Int. Cl.
*A61B 5/02* (2006.01)

(52) U.S. Cl. .................................................... 600/528

(58) Field of Classification Search ................ 600/514, 600/528, 586; 128/901; 381/67
See application file for complete search history.

(56) References Cited

U.S. PATENT DOCUMENTS

| 4,446,872 A | 5/1984 | Marsoner et al. |
| 4,546,777 A | 10/1985 | Groch et al. |
| 4,549,551 A | 10/1985 | Dyck et al. |
| 5,448,996 A | 9/1995 | Bellin et al. |
| 6,215,408 B1 * | 4/2001 | Leonard et al. ............. 340/644 |
| 6,245,025 B1 * | 6/2001 | Torok et al. ................ 600/500 |
| 6,643,548 B1 * | 11/2003 | Mai et al. ..................... 607/17 |

FOREIGN PATENT DOCUMENTS

WO    WO 99/384431    8/1999

OTHER PUBLICATIONS

Eric W. Weisstein. "First Derivative Test." From MathWorld—A Wolfram Web Resource. http://mathworld.wolfram.com/FirstDerivativeTest.html.*
Eric W. Weisstein. "Finite Difference." From MathWorld—A Wolfram Web Resource. http://mathworld.wolfram.com/FiniteDifference.html.*

* cited by examiner

*Primary Examiner*—Robert E. Pezzuto
*Assistant Examiner*—Brian T. Gedeon
(74) *Attorney, Agent, or Firm*—Wood, Phillips, Katz, Clark & Mortimer

(57) ABSTRACT

This invention concerns a method and system for automatically determining heart rate. The invention can be applied to determining the heart of any animal including humans. The method involves sensing body sounds and transducing them to electrical signals. Digitizing the electrical signals. Emphasizing the heart sound maxima (S1 and S2 signals) relative to noise by filtering, decompression and squaring. Detecting local maxima in the signals as likely S1 signals and generating a threshold amplitude. Selecting maxima that exceed the threshold as surviving likely candidate S1 signals. Screening the surviving candidate S1 against physiologically derived criteria. And, calculating the heart rate from the screened S1.

33 Claims, 5 Drawing Sheets

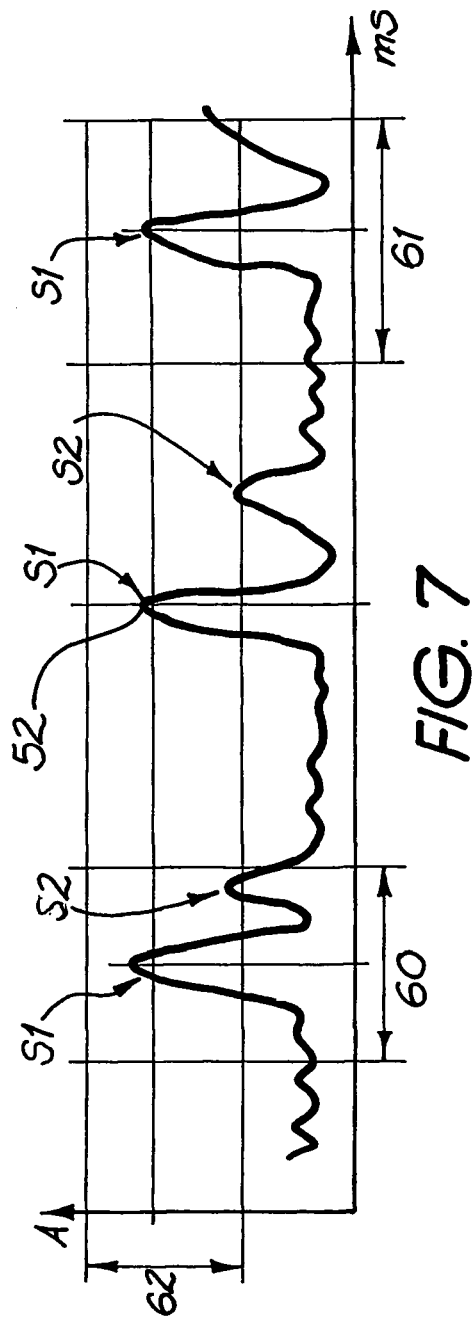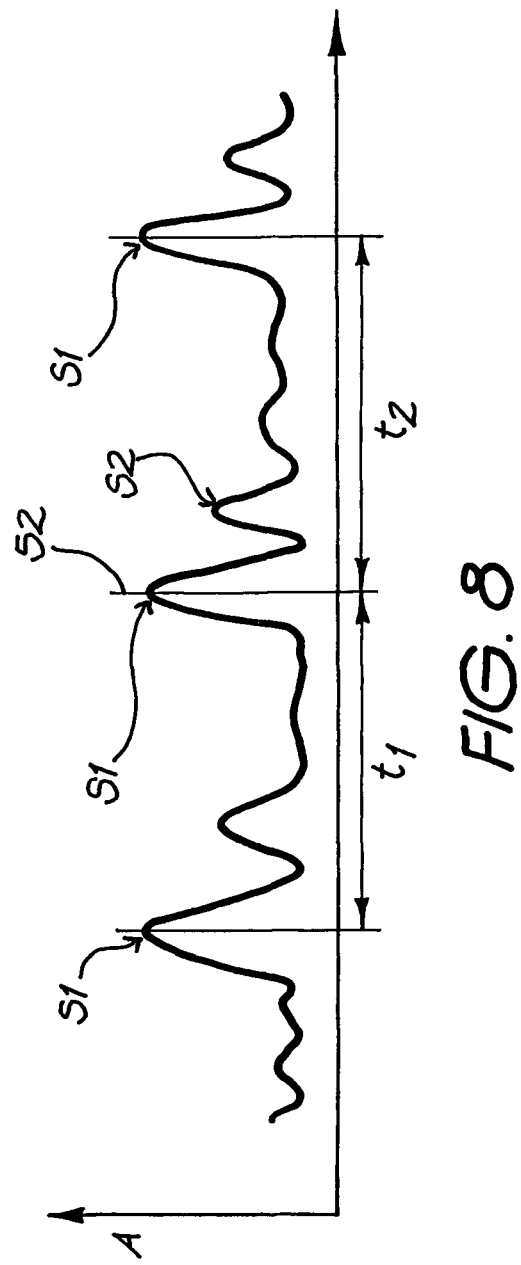

DETERMINING HEART RATE

TECHNICAL FIELD

This invention concerns a method and system for automatically determining heart rate. The invention can be applied to determining the heart of any animal including humans.

BACKGROUND ART

Vibration of the heart valves generates heart sounds. The valves are forced into vibration at the instants of the valves' closure, caused by abrupt increase of the blood pressure gradient. A first heart sound (S1) is generated at the end of diastole, while a second heart sound (S2) is produced at the end of the systole. The sounds are transmitted through the body and can be heard on the body surface by use of the stethoscope, or be recorded using a sound transducer. Although heart sounds have been recorded in the past, they have not been used to automatically determine heart rate. The major problem being that for each heart beat there are four sounds generated by valve closure, typically grouped in pairs.

SUMMARY OF THE INVENTION

The invention is a method for automatically determining heart rate, comprising the steps of:

Sensing body sounds and transducing them to electrical signals.

Digitizing the electrical signals.

Emphasising the heart sound maxima (S1 and S2 signals) relative to noise by filtering, decompression and squaring.

Detecting local maxima in the signals.

Generating a threshold amplitude.

Selecting maxima that exceed the threshold.

Screening selected maxima against physiologically derived criteria.

Calculating the heart rate from the screened maxima.

The digitizing involves the conventional sampling process to produce a string of digital words, one word for each sample.

The filtering may be performed using a first low pass filter having a cutoff at 60 Hz.

Further filtering may be performed after the decompression and squaring by a further low pass filter realised as a moving average FIR filter, and triangular weighting may be used instead of an equal weighting function.

Probable S1's and S2's may be selected from those parts of the signal detected to be around maximums.

Local maxima may be detected by differentiating the signal. The derivative may be calculated as the first order difference, with the signal at every point being subtracted from the signal delayed by one sample. The signal may be divided onto intervals, and the maximum with the greatest amplitude may be taken for each interval.

This maximum may be selected as a likely S1. If there is another maximum following in a suitable time window after the likely S1 in the same interval, then it may be selected to be a likely S2. The time window may be between 160 ms and 400 ms.

Once a string of likely S1's and S2's have been recorded four histograms may be constructed, namely histograms of the "S1 amplitudes", the "S2 amplitudes", the "S1 to S1 intervals" and the "S1 to S2 intervals".

A threshold amplitude may be generated for the likely S1's using the "S1 amplitudes" histogram. Any amplitude bin, or bins, on the histogram that show occurrence with a frequency greater than a physiologically derived upper limit, or threshold, are identified. then, all the amplitude bins are discarded except those that have an amplitude greater than the amplitude of the bin(s) that have been identified.

Once the likely S1's have been reduced the S2's are reduced to include only those detected in a predetermined time window after the surviving likely S1'. Then the histograms are updated to include only the surviving likely candidate S1's and S The surviving likely candidate S1's and S2's may then be tested against the following criteria:

If a candidate S1 is wider than 250 ms at 80% of its peak value, or wider than 350 ms at 50% of its peak value, it is rejected.

If other S1's are not found within an expected time window or amplitude window on both sides of a candidate S1, it is rejected. The time window may be derived from the histogram of "S1 to S1 intervals". The amplitude window may be derived from the histogram of "S1 amplitudes".

If the time since the preceding candidate S1 is less than the time until the next S1, the current candidate is presumed to be an S2, and it is rejected.

If the time since the preceding candidate S1 is less than the largest S1 to S2 interval, seen from the histogram of "S1 to S2 intervals", the current candidate is presumed to be S2, and it is rejected.

If the ratio of the amplitude of a candidate S1's to the amplitude of its S2's is smaller or bigger than an expected window, the candidate is rejected.

In another aspect the invention is a system for determining heart rate, comprising:

An array of sensors to pick up the sounds and transform them to electrical signals.

A computer to digitize the signals and process them to detect S1 and S2.

Where the processing may comprise:

Emphasizing the heart sound maxima (S1 and S2 signals) relative to noise by filtering, decompression and squaring.

Detecting local maxima in the signals.

Generating a threshold amplitude.

Selecting maxima that exceed the threshold.

Screening selected maxima against physiologically derived criteria.

Calculating the heart rate from the screened maxima.

BRIEF DESCRIPTION OF THE DRAWINGS

An example of the invention will now be described with reference to the accompanying drawings, in which:

FIG. 7 is a graph of the signals showing an S1 with another S1 before and after it, in respective amplitude and time windows.

FIG. 8 is the graph of FIG. 7 showing the times between successive S1 events.

BEST MODES OF THE INVENTION

Figure 1:
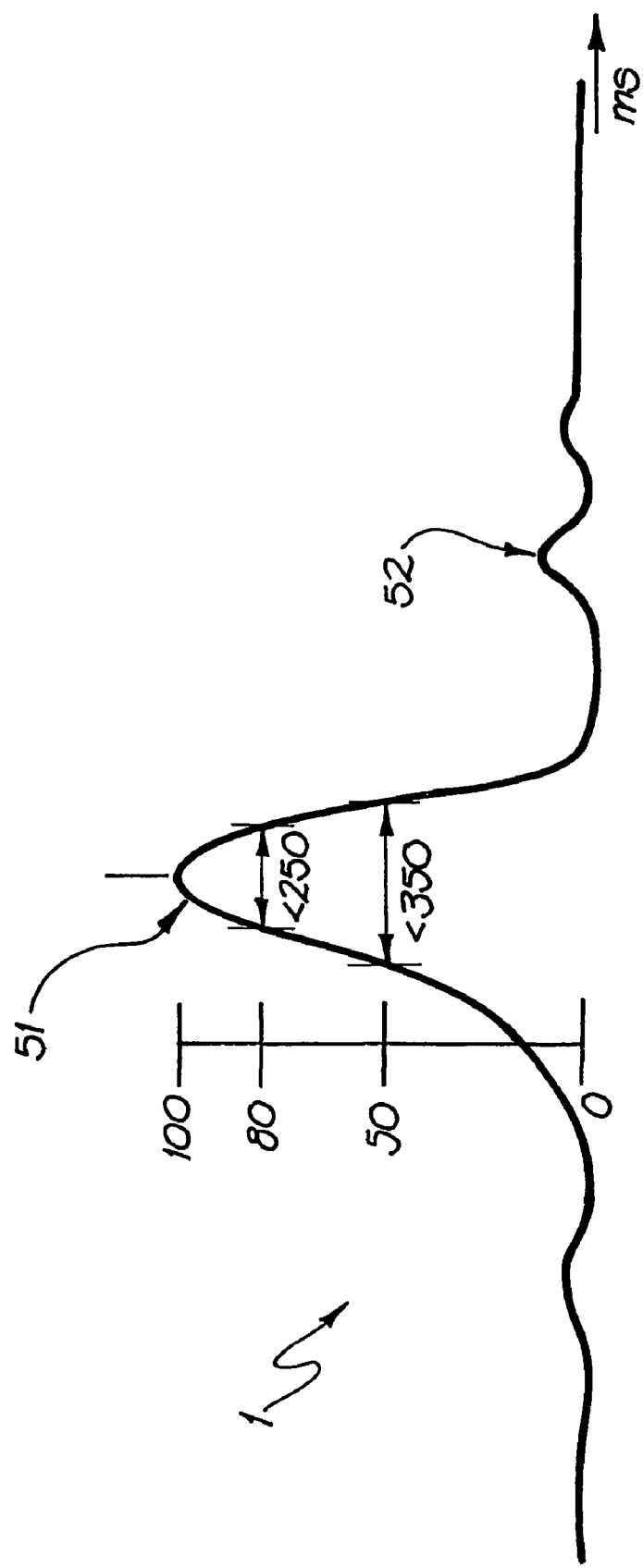
FIG. 1 is a diagram showing a typical cycle of heart sound.

Referring first to FIG. 1 a typical cycle of heart sound 1 is seen to comprise a first heart sound (S1) which is generated at the end of diastole, and a second heart sound (S2) which is produced at the end of the systole.

Figure 2:
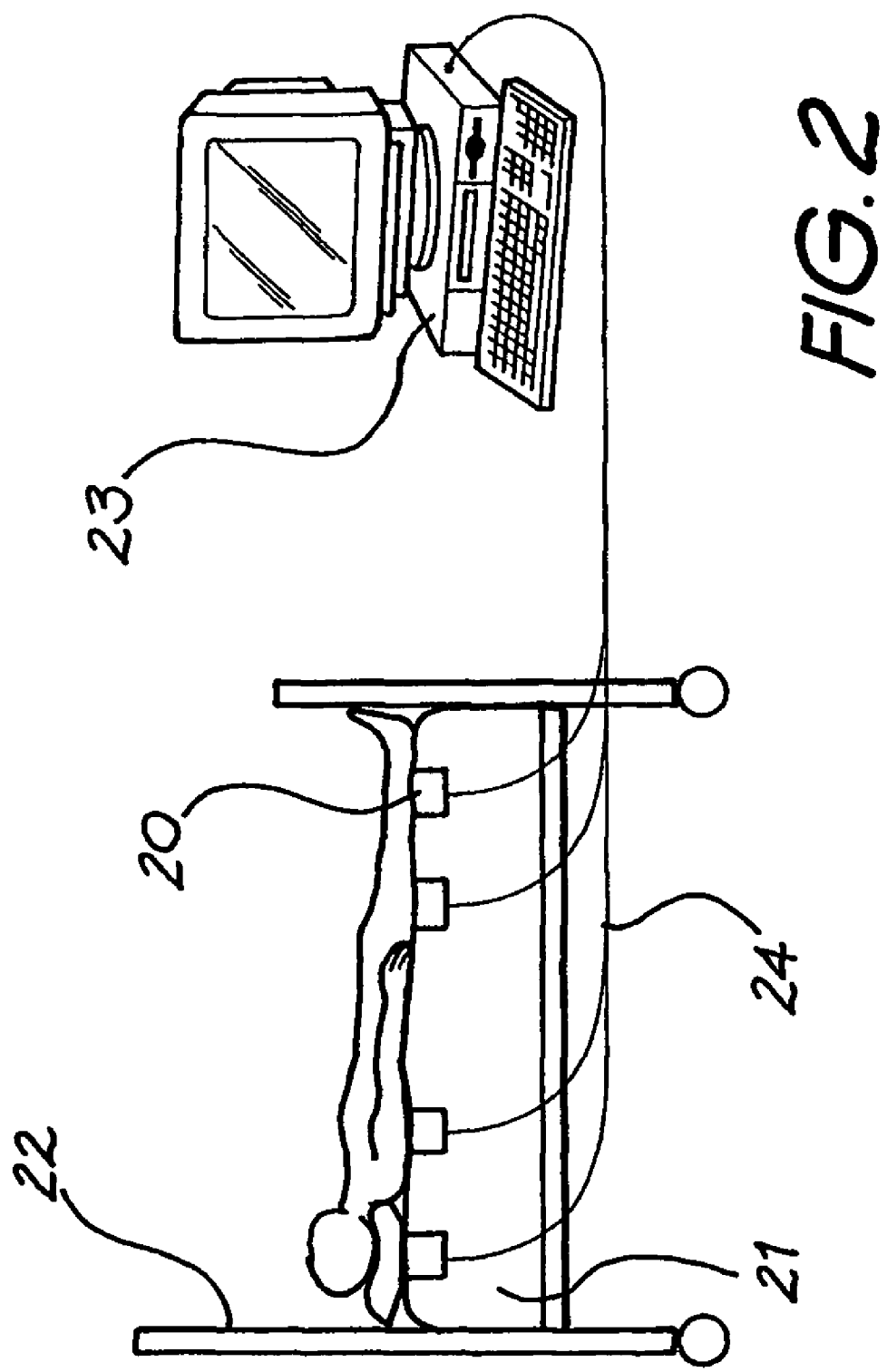
FIG. 2 is a schematic diagram of a system for monitoring heart rate.

Referring now to FIG. 2 an array of sensors 20 are arranged in the mattress 21 of a bed 22. The sensors 20 pick up the sounds and transduce them to electrical signals. The signals are passed to a computer 23, via cables 24, where they are sampled, digitized and processed by a computer program.

Figure 3:
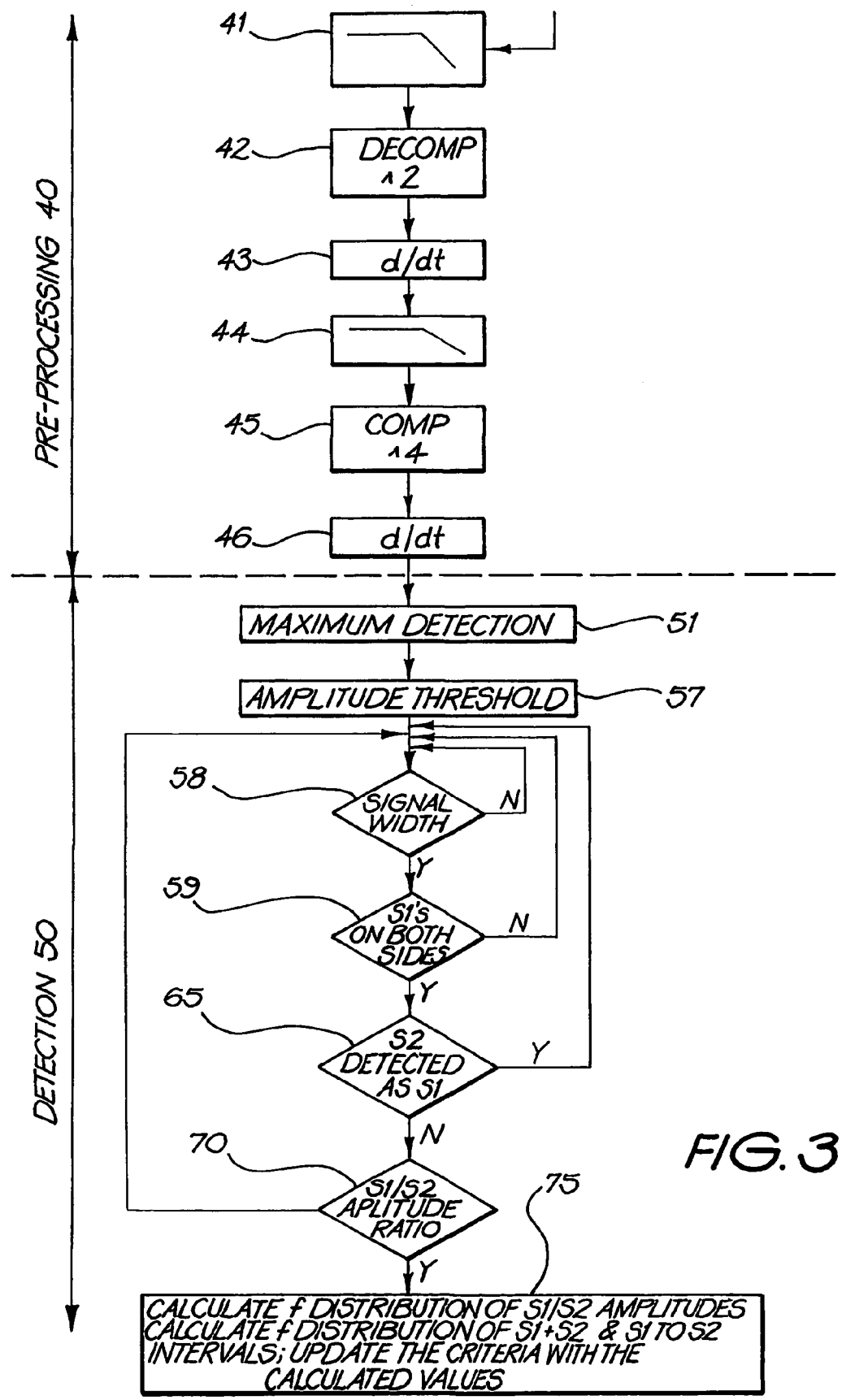
FIG. 3 is a flow chart of a method for monitoring heart rate.

Refer now to FIG. 3. The program then performs an algorithm 30 to detect the S1 and S2 in the signals. Once these are detected the heart rate can be calculated. The algorithm can be divided into two phases: preprocessing 40 and detection 50.

Pre-Processing Phase 40:

The purpose of this phase is to emphasize the S1 and S2 parts of the signal relative to the noise.

The signal is first low pass filtered 41 with a cutoff frequency (−3 dB) at 60 Hz, to attenuate high frequency noise.

The signal is then decompressed and then squared 42, in order to increase the amplitude difference.

The signal is then differentiated 43. The derivative is calculated as the first order difference between each sample, that is, the signal at every point is subtracted from the signal delayed by one sample.

Further low pass filtering 44 then attenuates the residual noise. This low pass filter is realised as a moving average FIR filter, and triangular weighting length of 180 is used instead of an equal weighting function.

The purpose of this phase is to emphasize the maxima in the signal relative to the noise. The resulting maxima at this point have characteristic accentuated shapes.

The signal is then compressed 45 and differentiated again 46.

The detection phase 50 consists of several parts:

i. Detecting Local Maxima 51:

The mathematical characteristic of a maximum is that the first derivative changes in sign from positive to negative, and the second derivative is zero. The algorithm 30 selects as likely S1's and S2's only a number of samples of the signal around a maxima.

A first likely S1 52 is selected at time $t_0$ to be the maximum of greatest amplitude in a predetermined spread 53 of 160 ms.

If another maximum 54 is detected within a predetermined time window 55 (160 to 450 ms) after the S1, then it 54 is selected to be likely S2.

Figure 4:
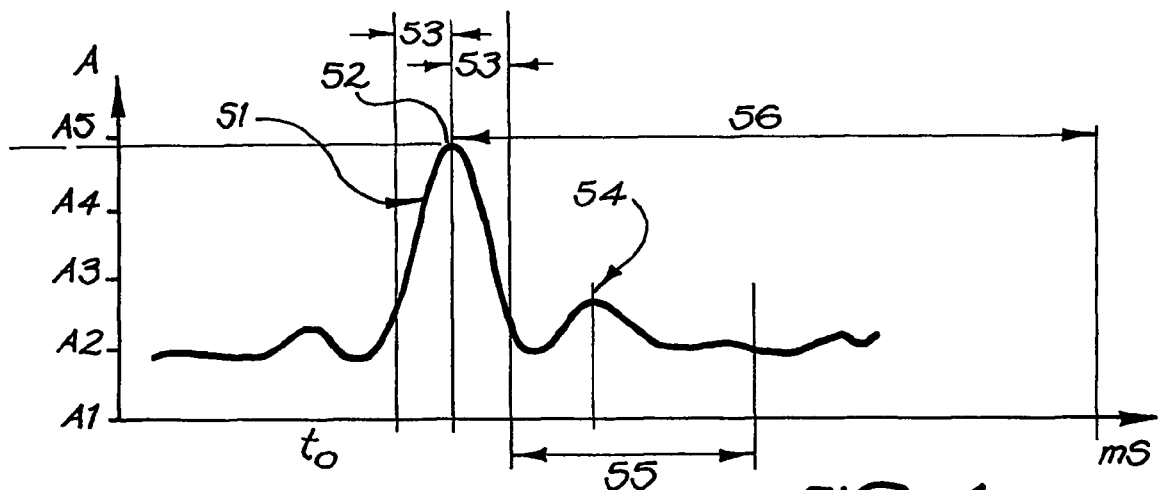
FIG. 4 is a graph of a filtered, decompressed and squared signal.

The next likely S1 is then selected to be the maximum of greatest amplitude in the next predetermined interval 56, and then the next likely S2 may then be selected. This is illustrated in FIG. 4.

Once some likely S1 and S2 are selected, their amplitudes are measured, and so are the "S1 to S time intervals" and the "S1 to S2 time intervals". These measurements are used to build four histograms, namely histograms of the "S1 amplitudes", the "S2 amplitudes", the "S1 to S1 intervals" and the "S1 to S2 intervals". These histograms are used to generate detection criteria for use in subsequent iterations.

Figure 5:
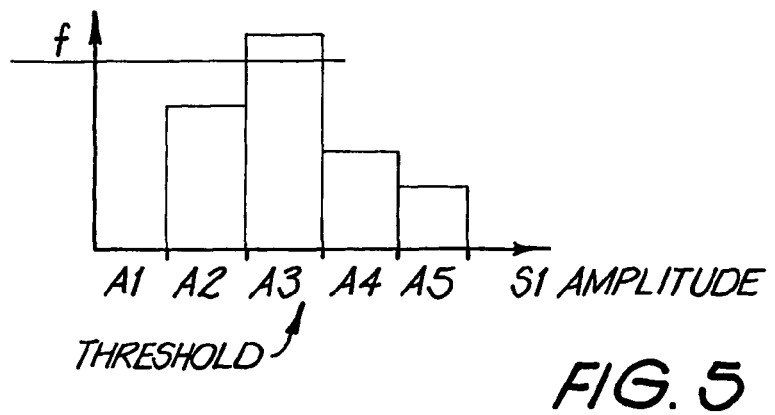
FIG. 5 is a histogram of S1 amplitudes.

For example, in FIG. 5 a histogram of S1 amplitudes has S1 52 occurring in the bin indicated.

ii. Amplitude Thresholding, 57

For the amplitude histograms there will generally always be the same number of bins; in the example shown in FIG. 5 there are five bins, A1, A2, A3, A4 and A5. The bin width (the resolution of the histogram) is calculated from the dynamic range of the signal, so where there is greater range the bins will be wider. The frequency 'f' of the occurrence of the maxima is given by the number of occurrences in each predetermined epoch of time, for example 30 secs.

There is an upper limit possible for the heart rate of any particular subject, so any likely S1 that occurs with a frequency greater than that upper limit $f_1$, can be discarded. The likely S1's are then reduced to include only those in the bins that have an amplitude greater than the amplitude of the bin(s) that exceed the threshold. In the example shown in FIG. 5, bin A3 has a frequency greater than $f_1$, so A3 is the amplitude threshold, and bins A1, A2 and A3 are discarded. Likely S1 52 remains a surviving likely candidate.

Once the likely S1's have been reduced, the S2's are reduced accordingly.

Figure 6:
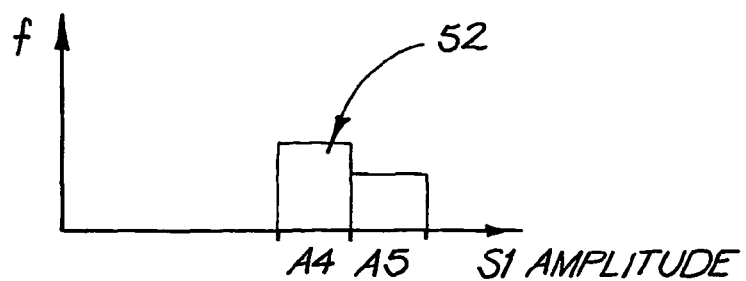
FIG. 6 is a histogram of S1 amplitudes that exceed a threshold.

The histograms are updated to include only the surviving likely candidates, as shown in FIG. 6.

iii. Screening Criteria

The above selection and thresholding provide necessary but not sufficient criteria for the unique identification of the S1 and S2. Further refinement is necessary. The following criteria have been developed from physiology and empirical investigation of the signals.

Signal Width Criteria, 58.

The width of the S1 at 80% and 50% of its peak has been determined from a number of studies. It is found that the width of the S1 is within 250 ms and 350 ms at 80% and 50% respectively. At any maximum, if the width of the signal is wider than this, the maximum is rejected as an S1; as shown in FIG. 1.

Requiring the existence of likely S1's on both sides of a new candidate S1, 59.

If likely S1's are not found in the expected time and amplitude windows on both sides of a new candidate S1, such as 52, that candidate S1 52 is rejected.

The algorithm searches the time windows before 60 and after 61 the possible S1, and an amplitude window 62 around the possible S1, as shown in FIG. 7. The time window (minimum and maximum intervals) and amplitude window (minimum and maximum) are determined from historically detected S1 events. This is done using the histograms of the "S1 to S1 intervals" and "S1 amplitudes".

Preventing S2's being detected as S1's, 65.

If a maximum is detected within a time $t_1$ which is less than the time $t_2$ to the next S1, that is if $t_1$ is less than $t_2$ as shown in FIG. 8, the maximum is presumed to be S2 and is discarded.

Also, using the "S1 to S2" intervals histogram, if a maximum is detected within a time $t_1$ less than the largest S1 to S2 intervals, the maximum is presumed to be S2 and is discarded.

The S1/S2 amplitude ratio 70.

Using the histograms of the "S1 amplitudes", and the "S2 amplitudes", a window of the smallest and largest amplitude ratios is constructed. The ratio of the amplitudes of a likely S1 and its S2 is checked against the window, and if the ratio is outside the window the maximum is rejected.

If a maxima satisfies all these criteria, the S1 and S2 heart signals are presumed detected. The time intervals "S1 to S1", "S1 to S2" as well as the "S1 amplitude" and "S2 amplitude" are measured, and the histograms are updated 75.

Once S1 and S2 are detected they are used to calculate the heart rate.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for automatically determining heart rate, comprising the steps of:
   sensing body sounds and transducing them to electrical signals;
   digitizing the electrical signals;
   emphasizing the heart sound maxima (S1 and S2 signals) relative to noise by a first filtering step, decompression and squaring;
   detecting local maxima in the signals as likely S1 signals;
   generating a threshold amplitude;
   selecting maxima that exceed the threshold as surviving likely candidate S1 signals;
   screening the surviving candidate S1 against physiologically derived criteria; and
   calculating the heart rate from the screened S1, wherein further filtering is performed after the decompression and squaring by a further low pass filter realised as a moving average FIR filter using triangular weighting.

2. A meted according to claim 1, where the first filtering step is performed using a first low pass filter having a cutoff at 60 Hz.

3. A method according to claim 1, where probable S1's and S2's are selected from those parts of the signal detected to be around maxima.

4. A method according to claim 1, where local maxima are detected by differentiating the signal.

5. A method according to claim 4, where the derivative is calculated as the first order difference.

6. A method for automatically determining heart rate, compromising the steps of:
   sensing body sounds and transducing them to electrical signals:
   digitizing the electrical signals;
   emphasizing the heart sound maxima (S1 and S2 signals) relative to noise by filtering, decompression and squaring;
   detecting local maxima in the signals as likely S1 signals by differentiating the signals;
   generating a threshold amplitude;
   selecting maxima that exceed the threshold as surviving likely candidate S1 signals;
   screening the surviving candidate S1 against physiologically derived criteria; and
   calculating the heart rate from the screened S1;
   where local maxima are detected by differentiating the signal and
   where the signal is divided onto intervals, and the maximum with the greatest amplitude is taken for each interval and selected to be a likely S1.

7. A method according to claim 6, where if there is another maximum following in a suitable time window after the likely S1 in the same interval, then it is selected to be a likely S2.

8. A method according to claim 7, where the time window is between 160 ms and 400 ms.

9. A method according to claim 6, where, once a string of likely S1's and S2's have been recorded four histograms are constructed, namely histograms of the "S1 amplitudes", the "S2 amplitudes", the "S1 to S1 intervals" and the "S1 to S2 intervals".

10. A method according to claim 6, where a threshold amplitude is generated for the likely S1's using an "S1 amplitudes" histogram, and where any amplitude bin, or bins, on the histogram that show occurrence with a frequency greater than a physiologically derived upper limit, or threshold, are identified, and then, all the amplitude bins are discarded except those that have an amplitude greater than the amplitude of the bin(s) that have been identified.

11. A method according to claim 10, where once the likely S1's have been reduced the S2's are reduced to include only those detected in a predetermined time window alter the surviving likely S1's, and then the histograms are updated to include only the surviving likely candidate S1's and S2's.

12. A method according to claim 11, where likely candidate S1's and S2's are tested against the following criteria:
    if a candidate S1 is wider than 250 ms at 80% of its peak value, or wider than 350 ms at 50% of its peak value, it is rejected.

13. A method according to claim 11, where likely candidate S1's and S2's are tested against the following criteria:
    if other S1's are not found within an expected time window or amplitude window on both sides of a candidate S1, it is rejected.

14. A method according to claim 13, where the time window is derived from a histogram of "S1 to S1 intervals".

15. A method according to claim 13, where the amplitude window is derived from a histogram of "SI amplitudes".

16. A method according to claim 11, where likely candidate S1's and S2's are tested against the following criteria:
    if the time since the preceding candidate S1 is less than the time until the next S1, the current candidate is presumed to be an S2, and it is rejected.

17. A method according to claim 11, where likely candidate S1's and S2's are tested against the following criteria:
    if the time since the preceding candidate S1 is less than the largest S1 to S2 interval, seen from the histogram of "S1 to S2 intervals", the current candidate is presumed to be S2, and it is rejected.

18. A method according to claim 11, where likely candidate S1's and S2's are tested against the following criteria:
    if the ratio of the amplitude of a candidate S1's to the amplitude of its S2's is smaller or bigger than an expected window, the candidate is rejected.

19. A method according to claim 1, wherein local maxima are detected by differentiating the signal and wherein the signal is divided onto intervals, and the maximum with the greatest amplitude is taken for each interval and selected to be a likely S1.

20. A method according to claim 19, where if there is another maximum following in a suitable time window after the likely S1 in the same interval, then it is selected to be a likely S2.

21. A method according to claim 20, where the time window is between 160 ms and 400 ms.

22. A method according to claim 19, where, once a string of likely S1's and S2's have been recorded four histograms are constructed, namely histograms of the "S1 amplitudes", the "S2 amplitudes", the "S1 to S1 intervals" and the "S1 to S2 intervals".

23. A method according to claim 19, where a threshold amplitude is generated for the likely S1's using an "S1 amplitudes" histogram, and where any amplitude bin, or bins, on the histogram that show occurrence with a frequency greater than a physiologically derived upper limit, or threshold, are identified, and then, all the amplitude bins are discarded except those that have an amplitude greater than the amplitude of the bin(s) that have been identified.

24. A system for determining heart rate, comprising an array of sensors to pick up the sounds and transform them to electrical signals, and a computer to digitize the signals and process them to detect S1 and S2, where the processing includes the steps of:
   sensing body sounds and transducing them to electrical signals;
   digitizing the electrical signals;
   emphasizing the heart sound maxima (S1 and S2 signals) relative to noise by filtering, decompression and squaring;
   detecting local maxima in the signals as likely S1 signals;
   generating a threshold amplitude;
   selecting maxima that exceed the threshold as surviving likely candidate S1 signals;
   screening the surviving candidate S1 against physiologically derived criteria; and
   calculating the heart rate from the screened S1;
   the system further comprising:
   a low pass filter realised as a moving average FIR filter using triangular weighting, to perform farther filtering after the decompression and squaring.

25. A system according to claim 24 further comprising a first low pass filter having a cutoff at 60 Hz to perform the filtering.

26. A method according to claim 23, where once the likely S1's have been reduced the S2's are reduced to include only those detected in a predetermined time window after the surviving likely S1's, and then the histograms are updated to include only the surviving likely candidate S1's and S2's.

27. A method according to claim 26, where likely candidate S1's and S2's are tested against the following criteria:
   if a candidate S1 is wider than 250 ms at 80% of its peak value, or wider than 350 ms at 50% of its peak value, it is rejected.

28. A method according to claim 26, where likely candidate S1's and S2's are tested against the following criteria:
   if other S1's are not found within an expected time window or amplitude window on both sides of a candidate S1, it is rejected.

29. A method according to claim 28, where the time window is derived from a histogram of "S1 to S1 intervals".

30. A method according to claim 28, where the amplitude window is derived from a histogram of "S1 amplitudes".

31. A method according to claim 27, where likely candidate S1's and S2's are tested against the following criteria:
   if the time since the preceding candidate S1 is less than the time until the next S1, the current candidate is presumed to be an S2, and it is rejected.

32. A method according to claim 26, where likely candidate S1's and S2's are tested against the following criteria:
   if the time since the preceding candidate S1 is less than the largest S1 to S2 interval, seen from the histogram of "S1 to S2 intervals", the current candidate is presumed to be S2, and it is rejected.

33. A method according to claim 26, where likely candidate S1's and S2's are tested against the following criteria:
   if the ratio of the amplitude of a candidate S1's to the amplitude of its S2's is smaller or bigger than an expected window, the candidate is rejected.

* * * * *